(12) United States Patent
Ou et al.

(10) Patent No.: US 10,132,793 B2
(45) Date of Patent: Nov. 20, 2018

(54) DROPOUT DETECTION IN CONTINUOUS ANALYTE MONITORING DATA DURING DATA EXCURSIONS

(71) Applicant: Abbott Diabetes Care Inc., Alameda, CA (US)

(72) Inventors: Junli Ou, Pleasanton, CA (US); Erwin Satrya Budiman, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 544 days.

(21) Appl. No.: 14/424,026

(22) PCT Filed: Aug. 20, 2013

(86) PCT No.: PCT/US2013/055883
§ 371 (c)(1),
(2) Date: Feb. 25, 2015

(87) PCT Pub. No.: WO2014/035732
PCT Pub. Date: Mar. 6, 2014

(65) Prior Publication Data
US 2015/0241407 A1  Aug. 27, 2015

Related U.S. Application Data

(60) Provisional application No. 61/695,164, filed on Aug. 30, 2012.

(51) Int. Cl.
*G01N 33/49* (2006.01)
*A61B 5/145* (2006.01)
(Continued)

(52) U.S. Cl.
CPC ......... *G01N 33/49* (2013.01); *A61B 5/14532* (2013.01); *G06F 17/30958* (2013.01);
(Continued)

(58) Field of Classification Search
CPC .... G01N 33/49; G16H 10/60; A61B 5/14532; G06F 17/30958
(Continued)

(56) References Cited

U.S. PATENT DOCUMENTS 3,581,062 A   5/1971  Aston
3,926,760 A   12/1975 Allen et al.
(Continued)

FOREIGN PATENT DOCUMENTS

EP   0098592   1/1984
EP   0127958   12/1984
(Continued)

OTHER PUBLICATIONS

European Patent Application No. 13833061.8, Examination Report dated Jan. 27, 2017.
(Continued)

*Primary Examiner* — Harry W Byrne
(74) *Attorney, Agent, or Firm* — Jackson & Co., LLP

(57) ABSTRACT

Methods, devices, and systems are provided for identifying dropouts in analyte monitoring system sensor data including segmenting sensor data into a plurality of time series wherein each time series is associated with a different instance of a repeating event, selecting a first time series to analyze for dropouts from the plurality of time series; comparing the selected first time series to a second time series among the plurality of time series, determining whether the selected first time series includes a portion that is more than a predefined threshold lower than a corresponding portion of the second time series, and displaying, on a computer system display, an indication that the selected first time series includes a dropout if the selected first time series
(Continued)

includes a portion that is more than the predefined threshold lower than the corresponding portion of the second time series.

20 Claims, 10 Drawing Sheets

(51) Int. Cl.
    *G06F 17/30*     (2006.01)
    *G06K 9/00*     (2006.01)
    *G16H 10/60*     (2018.01)

(52) U.S. Cl.
    CPC .......... *G06K 9/0055* (2013.01); *G16H 10/60* (2018.01); *A61B 2560/0276* (2013.01)

(58) Field of Classification Search
    USPC ........................................................ 702/104
    See application file for complete search history.

(56) References Cited

U.S. PATENT DOCUMENTS

| | | |
|---|---|---|
| 3,949,388 A | 4/1976 | Fuller |
| 3,960,497 A | 6/1976 | Acord et al. |
| 4,033,330 A | 7/1977 | Willis et al. |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,431,004 A | 2/1984 | Bessman et al. |
| 4,441,968 A | 4/1984 | Emmer et al. |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,204,264 A | 4/1993 | Kaminer et al. |
| 5,210,778 A | 5/1993 | Massart |
| 5,228,449 A | 7/1993 | Christ et al. |
| 5,231,988 A | 8/1993 | Wernicke et al. |
| 5,243,696 A | 9/1993 | Carr et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,532,686 A | 7/1996 | Urbas et al. |
| 5,552,997 A | 9/1996 | Massart |
| 5,555,190 A | 9/1996 | Derby et al. |
| 5,564,434 A | 10/1996 | Halperin et al. |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,324 A | 5/1997 | Sarbach |
| 5,634,468 A | 6/1997 | Platt et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,724,030 A | 3/1998 | Urbas et al. |
| 5,726,646 A | 3/1998 | Bane et al. |
| 5,733,259 A | 3/1998 | Valcke et al. |
| 5,735,285 A | 4/1998 | Albert et al. |
| 5,748,103 A | 5/1998 | Flach et al. |
| 5,749,907 A | 5/1998 | Mann |
| 5,772,586 A | 6/1998 | Heinonen et al. |
| 5,791,344 A | 8/1998 | Schulman et al. |
| 5,804,047 A | 9/1998 | Karube et al. |
| 5,833,603 A | 11/1998 | Kovacs et al. |
| 5,842,189 A | 11/1998 | Keeler et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,919,141 A | 7/1999 | Money et al. |

(56) References Cited

U.S. PATENT DOCUMENTS

| | | |
|---|---|---|
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,708 A | 11/1999 | Champagne et al. |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,130,623 A | 10/2000 | MacLellan et al. |
| 6,134,461 A | 10/2000 | Say et al. |
| 6,143,164 A | 11/2000 | Heller et al. |
| 6,144,871 A | 11/2000 | Saito et al. |
| 6,157,850 A | 12/2000 | Diab et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,347 B1 | 10/2001 | Pompei |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,046 B1 | 11/2002 | Say et al. |
| 6,493,069 B1 | 12/2002 | Nagashimada et al. |
| 6,496,729 B2 | 12/2002 | Thompson |
| 6,497,655 B1 | 12/2002 | Linberg et al. |
| 6,498,043 B1 | 12/2002 | Schulman et al. |
| 6,514,718 B1 | 2/2003 | Heller et al. |
| 6,520,326 B2 | 2/2003 | McIvor et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,631,281 B1 | 10/2003 | Kastle |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |
| 6,730,025 B1 | 5/2004 | Platt |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,740,075 B2 | 5/2004 | Lebel et al. |
| 6,740,518 B1 | 5/2004 | Duong et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B2 | 8/2004 | Schaupp et al. |
| 6,789,195 B1 | 9/2004 | Prihoda et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |

(56) References Cited

U.S. PATENT DOCUMENTS

| | | |
|---|---|---|
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman, IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,011,630 B2 | 3/2006 | Desai et al. |
| 7,015,817 B2 | 3/2006 | Copley et al. |
| 7,016,713 B2 | 3/2006 | Gardner et al. |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,305 B2 | 5/2006 | KenKnight et al. |
| 7,046,153 B2 | 5/2006 | Oja et al. |
| 7,052,472 B1 | 5/2006 | Miller et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,167,818 B2 | 1/2007 | Brown |
| 7,171,274 B2 | 1/2007 | Starkweather et al. |
| 7,174,199 B2 | 2/2007 | Berner et al. |
| 7,179,226 B2 | 2/2007 | Crothall et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,711,493 B2 | 5/2010 | Bartkowiak et al. |
| 7,713,574 B2 | 5/2010 | Brister et al. |
| 7,715,893 B2 | 5/2010 | Kamath et al. |
| 7,736,310 B2 | 6/2010 | Taub et al. |
| 7,741,734 B2 | 6/2010 | Joannopoulos et al. |
| 7,751,864 B2 | 7/2010 | Buck, Jr. |
| 7,766,829 B2 | 8/2010 | Sloan et al. |
| 7,768,386 B2 | 8/2010 | Hayter et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,775,444 B2 | 8/2010 | DeRocco et al. |

(56) References Cited

U.S. PATENT DOCUMENTS

| | | |
|---|---|---|
| 7,778,680 B2 | 8/2010 | Goode et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,831,310 B2 | 11/2010 | Lebel et al. |
| 7,857,760 B2 | 12/2010 | Brister et al. |
| 7,860,574 B2 | 12/2010 | Von Arx et al. |
| 7,882,611 B2 | 2/2011 | Shah et al. |
| 7,885,697 B2 | 2/2011 | Brister et al. |
| 7,889,069 B2 | 2/2011 | Fifolt et al. |
| 7,899,511 B2 | 3/2011 | Shults et al. |
| 7,899,545 B2 | 3/2011 | John |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,920,906 B2 | 4/2011 | Goode et al. |
| 7,928,850 B2 | 4/2011 | Hayter et al. |
| 7,938,797 B2 | 5/2011 | Estes |
| 7,941,200 B2 | 5/2011 | Weinert et al. |
| 7,946,984 B2 | 5/2011 | Brister et al. |
| 7,946,985 B2 | 5/2011 | Mastrototaro et al. |
| 7,955,258 B2 | 6/2011 | Goscha et al. |
| 7,970,448 B2 | 6/2011 | Shults et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 7,996,158 B2 | 8/2011 | Hayter et al. |
| 7,999,674 B2 | 8/2011 | Kamen |
| 8,005,524 B2 | 8/2011 | Brauker et al. |
| 8,010,174 B2 | 8/2011 | Goode et al. |
| 8,010,256 B2 | 8/2011 | Oowada |
| 8,060,173 B2 | 11/2011 | Goode, Jr. et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,103,471 B2 | 1/2012 | Hayter |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,900 B2 | 4/2012 | Taub et al. |
| 8,170,803 B2 | 5/2012 | Kamath et al. |
| 8,179,266 B2 | 5/2012 | Hermle |
| 8,192,394 B2 | 6/2012 | Estes et al. |
| 8,216,138 B1 | 7/2012 | McGarraugh et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,282,549 B2 | 10/2012 | Brauker et al. |
| 8,374,668 B1 | 2/2013 | Hayter et al. |
| 8,376,945 B2 | 2/2013 | Hayter et al. |
| 8,377,271 B2 | 2/2013 | Mao et al. |
| 8,409,093 B2 | 4/2013 | Bugler |
| 8,444,560 B2 | 5/2013 | Hayter et al. |
| 8,461,985 B2 | 6/2013 | Fennell et al. |
| 8,478,557 B2 | 7/2013 | Hayter et al. |
| 8,484,005 B2 | 7/2013 | Hayter et al. |
| 8,543,354 B2 | 9/2013 | Luo et al. |
| 8,560,038 B2 | 10/2013 | Hayter et al. |
| 8,571,808 B2 | 10/2013 | Hayter |
| 8,583,205 B2 | 11/2013 | Budiman et al. |
| 8,597,570 B2 | 12/2013 | Terashima et al. |
| 8,600,681 B2 | 12/2013 | Hayter et al. |
| 8,612,163 B2 | 12/2013 | Hayter et al. |
| 8,657,746 B2 | 2/2014 | Roy |
| 8,682,615 B2 | 3/2014 | Hayter et al. |
| 8,710,993 B2 | 4/2014 | Hayter et al. |
| 8,834,366 B2 | 9/2014 | Hayter et al. |
| 8,845,536 B2 | 9/2014 | Brauker et al. |
| 9,060,719 B2 | 6/2015 | Hayter et al. |
| 9,289,179 B2 | 3/2016 | Hayter et al. |
| 9,398,872 B2 | 7/2016 | Hayter et al. |
| 9,408,566 B2 | 8/2016 | Hayter et al. |
| 9,439,586 B2 | 9/2016 | Bugler |
| 9,483,608 B2 | 11/2016 | Hayter et al. |
| 9,558,325 B2 | 1/2017 | Hayter et al. |
| 9,743,872 B2 | 8/2017 | Hayter et al. |
| 2001/0037366 A1 | 11/2001 | Webb et al. |
| 2002/0016534 A1 | 2/2002 | Trepagnier et al. |
| 2002/0019022 A1 | 2/2002 | Dunn et al. |
| 2002/0042090 A1 | 4/2002 | Heller et al. |
| 2002/0054320 A1 | 5/2002 | Ogino |
| 2002/0065454 A1 | 5/2002 | Lebel et al. |
| 2002/0068860 A1 | 6/2002 | Clark |
| 2002/0072784 A1 | 6/2002 | Sheppard et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0117639 A1 | 8/2002 | Paolini et al. |
| 2002/0120186 A1 | 8/2002 | Keimel |
| 2002/0128594 A1 | 9/2002 | Das et al. |
| 2002/0147135 A1 | 10/2002 | Schnell |
| 2002/0150959 A1 | 10/2002 | Lejeunne et al. |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0168338 A1 | 9/2003 | Gao et al. |
| 2003/0176933 A1 | 9/2003 | Lebel et al. |

(56) References Cited

U.S. PATENT DOCUMENTS

| | | |
|---|---|---|
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0034289 A1 | 2/2004 | Teller et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNuzzio et al. |
| 2004/0099529 A1 | 5/2004 | Mao et al. |
| 2004/0106858 A1 | 6/2004 | Say et al. |
| 2004/0111017 A1 | 6/2004 | Say et al. |
| 2004/0117204 A1 | 6/2004 | Mazar et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138588 A1 | 7/2004 | Saikley et al. |
| 2004/0142403 A1 | 7/2004 | Hetzel et al. |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0162678 A1 | 8/2004 | Hetzel et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | MacE |
| 2005/0001024 A1 | 1/2005 | Kusaka et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0070774 A1 | 3/2005 | Addison et al. |
| 2005/0070777 A1 | 3/2005 | Cho et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0112169 A1 | 5/2005 | Brauker et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0134731 A1 | 6/2005 | Lee et al. |
| 2005/0137530 A1 | 6/2005 | Campbell et al. |
| 2005/0143635 A1 | 6/2005 | Kamath et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0197793 A1 | 9/2005 | Baker, Jr. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0272985 A1 | 12/2005 | Kotulla et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0079740 A1 | 4/2006 | Silver et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0155180 A1 | 7/2006 | Brister et al. |

(56) References Cited

U.S. PATENT DOCUMENTS

| | | |
|---|---|---|
| 2006/0156796 A1 | 7/2006 | Burke et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee et al. |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0247508 A1 | 11/2006 | Fennell |
| 2006/0247710 A1 | 11/2006 | Goetz et al. |
| 2006/0247985 A1 | 11/2006 | Liamos et al. |
| 2006/0253296 A1 | 11/2006 | Liisberg et al. |
| 2006/0258929 A1 | 11/2006 | Goode et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027507 A1 | 2/2007 | Burdett et al. |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0055799 A1 | 3/2007 | Koehler et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0094216 A1 | 4/2007 | Mathias et al. |
| 2007/0100222 A1 | 5/2007 | Mastrototaro et al. |
| 2007/0106135 A1 | 5/2007 | Sloan et al. |
| 2007/0118030 A1 | 5/2007 | Bruce et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0151869 A1 | 7/2007 | Heller et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0191702 A1 | 8/2007 | Yodfat et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213657 A1 | 9/2007 | Jennewine et al. |
| 2007/0228071 A1 | 10/2007 | Kamen et al. |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0271285 A1 | 11/2007 | Eichorn et al. |
| 2007/0282299 A1 | 12/2007 | Hellwig |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0012701 A1 | 1/2008 | Kass et al. |
| 2008/0017522 A1 | 1/2008 | Heller et al. |
| 2008/0018433 A1 | 1/2008 | Pitt-Pladdy |
| 2008/0021436 A1 | 1/2008 | Wolpert et al. |
| 2008/0021666 A1 | 1/2008 | Goode, Jr. et al. |
| 2008/0021972 A1 | 1/2008 | Huelskamp et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0064943 A1 | 3/2008 | Talbot et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0114228 A1 | 5/2008 | McCluskey et al. |
| 2008/0119705 A1 | 5/2008 | Patel et al. |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0182537 A1 | 7/2008 | Manku et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |

(56) References Cited

U.S. PATENT DOCUMENTS

| | | |
|---|---|---|
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319085 A1 | 12/2008 | Wright et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | Van Antwerp et al. |
| 2009/0063187 A1 | 3/2009 | Johnson et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub et al. |
| 2009/0093687 A1 | 4/2009 | Telfort et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105568 A1 | 4/2009 | Bugler |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112478 A1 | 4/2009 | Mueller, Jr. et al. |
| 2009/0112626 A1 | 4/2009 | Talbot et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149728 A1 | 6/2009 | Van Antwerp et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |

(56) References Cited

U.S. PATENT DOCUMENTS

| | | |
|---|---|---|
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0259118 A1 | 10/2009 | Feldman et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292188 A1 | 11/2009 | Hoss et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022988 A1 | 1/2010 | Wochner et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0056992 A1 | 3/2010 | Hayter et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0064764 A1 | 3/2010 | Hayter et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0094111 A1 | 4/2010 | Heller et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121167 A1 | 5/2010 | McGarraugh et al. |
| 2010/0121169 A1 | 5/2010 | Petisce et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213080 A1 | 8/2010 | Celentano et al. |
| 2010/0230285 A1 | 9/2010 | Hoss et al. |
| 2010/0234710 A1 | 9/2010 | Budiman et al. |
| 2010/0240975 A1 | 9/2010 | Goode et al. |
| 2010/0261987 A1 | 10/2010 | Kamath et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0312176 A1 | 12/2010 | Lauer et al. |
| 2010/0313105 A1 | 12/2010 | Nekoomaram et al. |
| 2011/0004085 A1 | 1/2011 | Mensinger et al. |
| 2011/0004276 A1 | 1/2011 | Blair et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0040163 A1 | 2/2011 | Telson et al. |
| 2011/0054282 A1 | 3/2011 | Nekoomaram et al. |
| 2011/0060530 A1 | 3/2011 | Fennell |
| 2011/0077490 A1 | 3/2011 | Simpson et al. |
| 2011/0077494 A1 | 3/2011 | Doniger et al. |
| 2011/0081726 A1* | 4/2011 | Berman ............ A61B 5/0031 436/95 |
| 2011/0112696 A1 | 5/2011 | Yodfat et al. |
| 2011/0148905 A1 | 6/2011 | Simmons et al. |
| 2011/0152637 A1 | 6/2011 | Kateraas et al. |
| 2011/0208027 A1 | 8/2011 | Wagner et al. |
| 2011/0213225 A1 | 9/2011 | Bernstein et al. |
| 2011/0257895 A1 | 10/2011 | Brauker et al. |
| 2011/0282327 A1 | 11/2011 | Kellogg et al. |
| 2011/0287528 A1 | 11/2011 | Fern et al. |
| 2011/0289497 A1 | 11/2011 | Kiaie et al. |
| 2011/0320130 A1 | 12/2011 | Valdes et al. |
| 2011/0320167 A1 | 12/2011 | Budiman |
| 2012/0078071 A1 | 3/2012 | Bohm et al. |
| 2012/0088995 A1 | 4/2012 | Fennell et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0190989 A1 | 7/2012 | Kaiser et al. |
| 2012/0245447 A1 | 9/2012 | Karan et al. |
| 2013/0035575 A1 | 2/2013 | Mayou et al. |
| 2013/0184547 A1 | 7/2013 | Taub et al. |
| 2013/0225959 A1 | 8/2013 | Bugler |
| 2013/0231541 A1 | 9/2013 | Hayter et al. |
| 2013/0235166 A1 | 9/2013 | Jones et al. |
| 2013/0324823 A1 | 12/2013 | Koski et al. |
| 2014/0005499 A1 | 1/2014 | Catt et al. |
| 2014/0046160 A1 | 2/2014 | Terashima et al. |
| 2014/0121480 A1 | 5/2014 | Budiman et al. |
| 2014/0121488 A1 | 5/2014 | Budiman |
| 2015/0216456 A1 | 8/2015 | Budiman |
| 2016/0022221 A1 | 1/2016 | Ou et al. |

FOREIGN PATENT DOCUMENTS

| | | |
|---|---|---|
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| WO | WO-1993/006237 | 4/1993 |
| WO | WO-1996/025089 | 8/1996 |
| WO | WO-1996/035370 | 11/1996 |
| WO | WO-1998/035053 | 8/1998 |
| WO | WO-1999/056613 | 11/1999 |
| WO | WO-2000/049940 | 8/2000 |
| WO | WO-2000/059370 | 10/2000 |
| WO | WO-2000/074753 | 12/2000 |
| WO | WO-2000/078992 | 12/2000 |
| WO | WO-2001/052935 | 7/2001 |
| WO | WO-2001/054753 | 8/2001 |
| WO | WO-2002/016905 | 2/2002 |
| WO | WO-2002/058537 | 8/2002 |
| WO | WO-2003/000125 | 1/2003 |

(56) References Cited

FOREIGN PATENT DOCUMENTS

| WO | WO-2003/076893 | 9/2003 |
|---|---|---|
| WO | WO-2003/082091 | 10/2003 |
| WO | WO-2003/085372 | 10/2003 |
| WO | WO-2004/047445 | 6/2004 |
| WO | WO-2004/061420 | 7/2004 |
| WO | WO-2005/010756 | 2/2005 |
| WO | WO-2005/040404 | 5/2005 |
| WO | WO-2005/089103 | 9/2005 |
| WO | WO-2006/024671 | 3/2006 |
| WO | WO-2006/051466 | 5/2006 |
| WO | WO-2006/064397 | 6/2006 |
| WO | WO-2006/079114 | 7/2006 |
| WO | WO-2006/085087 | 8/2006 |
| WO | WO-2006/118947 | 11/2006 |
| WO | WO-2007/007459 | 1/2007 |
| WO | WO-2007/097754 | 8/2007 |
| WO | WO-2008/052057 | 5/2008 |
| WO | WO-2008/086541 | 7/2008 |
| WO | WO-2010/022387 | 2/2010 |
| WO | WO-2010/054408 | 5/2010 |
| WO | WO-2010/077329 | 7/2010 |

OTHER PUBLICATIONS

Hovorka, R., et al., "Nonlinear Model Predictive Control of Glucose Concentration in Subjects with Type 1 Diabetes", *Physiological Measurement*, vol. 55, Jul. 2004, pp. 905-920.
Steil, G. M., et al., "Closed-Loop Insulin Delivery—the Path of Physiological Glucose Control", *Advanced Drug Delivery Reviews*, vol. 56, 2004, pp. 125-144.
Steil, G. M., et al., "Determination of Plasma Glucose During Rapid Glucose Excursions with a Subcutaneous Glucose Sensor", *Diabetes Technology & Therapeutics*, vol. 5, No. 1, 2003, pp. 27-31.
Kovatchev, B. P., et al., "Graphical and Numerical Evaluation of Continuous Glucose Sensing Time Lag", *Diabetes Technology & Therapeutics*, vol. 11, No. 3, 2009, pp. 139-143.
European Patent Application No. 13833061.8, Extended European Search Report dated Mar. 15, 2016.
PCT Application No. PCT/US13/055883, International Search Report and Written Opinion of the International Searching Authority dated Jan. 27, 2014.
PCT Application No. PCT/US13/055883, International Preliminary Report on Patentability and Written Opinion of the International Searching Authority dated Mar. 12, 2015.
Armour, J. C., et al., "Application of Chronic Intravascular Blood Glucose Sensor in Dogs", *Diabetes*, vol. 39, 1990, pp. 1519-1526.
Arnold, M. A., et al., "Selectivity Assessment of Noninvasive Glucose Measurements Based on Analysis of Multivariate Calibration Vectors", *Journal of Diabetes Science and Technology*, vol. 1, No. 4, 2007, pp. 454-462.
Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1070.
Bennion, N., et al., "Alternate Site Glucose Testing: A Crossover Design", *Diabetes Technology & Therapeutics*, vol. 4, No. 1, 2002, pp. 25-33.
Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.
Boyne, M. S., et al., "Timing of Changes in Interstitial and Venous Blood Glucose Measured With a Continuous Subcutaneous Glucose Sensor", *Diabetes*, vol. 52, Nov. 2003, pp. 2790-2794.
Bremer, T. M., et al., "Benchmark Data from the Literature for Evaluation of New Glucose Sensing Technologies", *Diabetes Technology & Therapeutics*, vol. 3, No. 3, 2001, pp. 409-418.
Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.
Cheyne, E. H., et al., "Perfaimance of a Continuous Glucose Monitoring System During Controlled Hypoglycaemia in Healthy Volunteers", *Diabetes Technology & Therapeutics*, vol. 4, No. 5, 2002, pp. 607-613.
Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.
El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.
Eren-Oruklu, M., et al., "Estimation of Future Glucose Concentrations with Subject-Specific Recursive Linear Models", *Diabetes Technology & Therapeutics* vol. 11(4), 2009, pp. 243-253.
Feldman, B., et al., "A Continuous Glucose Sensor Based on Wired Enzyme™ Technology Results from a 3-Day Trial in Patients with Type 1 Diabetes", *Diabetes Technology & Therapeutics*, vol. 5, No. 5, 2003, pp. 769-779.
Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.
Garg, S., et al., "Improvement in Glycemic Excursions with a Transcutaneous, Real-Time Continuous Glucose Sensor", *Diabetes Care*, vol. 29, No. 1, 2006, pp. 44-50.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, P. C., "Peripheral Circulation", *John Wiley & Sons*, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Kuure-Kinsey, M., et al., "A Dual-Rate Kalman Filter for Continuous Glucose Monitoring", *Proceedings of the 28th IEEE, EMBS Annual International Conference*, New York City, 2006, pp. 63-66.
Li, Y., et al., "In Vivo Release From a Drug Delivery MEMS Device", *Journal of Controlled Release*, vol. 100, 2004, pp. 211-219.
Lo, B., et al., "Key Technical Challenges and Current Implementations of Body Sensor Networks", *Body Sensor Networks*, 2005, pp. 1-5.
Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.
Lortz, J., et al., "What is Bluetooth? We Explain the Newest Short-Range Connectivity Technology", *Smart Computing Learning Series, Wireless Computing*, vol. 8, Issue 5, 2002, pp. 72-74.
Malin, S. F., et al., "Noninvasive Prediction of Glucose by Near-Infrared Diffuse Reflectance Spectroscopy", *Clinical Chemistry*, vol. 45, No. 9, 1999, pp. 1651-1658.
McGarraugh, G., et al., "Glucose Measurements Using Blood Extracted from the Forearm and the Finger", *TheraSense, Inc.*, 2001, 16 Pages.
McGarraugh, G., et al., "Physiological Influences on Off-Finger Glucose Testing", *Diabetes Technology & Therapeutics*, vol. 3, No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

(56) References Cited

OTHER PUBLICATIONS

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Panteleon, A. E., et al., "The Role of the Independent Variable to Glucose Sensor Calibration", *Diabetes Technology & Therapeutics*, vol. 5, No. 3, 2003, pp. 401-410.

Parker, R., et al., "Robust Hoo Glucose Control in Diabetes Using a Physiological Model", *AIChE Journal*, vol. 46, No. 12, 2000, pp. 2537-2549.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Rodriguez, N., et al., "Flexible Communication and Control Protocol for Injectable Neuromuscular Interfaces", *IEEE Transactions on Biomedical Circuits and Systems*, vol. 1, No. 1, 2007, pp. 19-27.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

European Patent Application No. 18164134.1, Extended European Search Report dated Aug. 1, 2018.

\* cited by examiner

DROPOUT DETECTION IN CONTINUOUS ANALYTE MONITORING DATA DURING DATA EXCURSIONS

CROSS-REFERENCE TO RELATED APPLICATIONS

This national stage patent application under 35 U.S.C. § 371 claims priority to PCT Application No. PCT/US2013/055883 filed Aug. 20, 2013, which claims priority to U.S. Provisional Patent Application Ser. No. 61/695,164, filed on Aug. 30, 2012, entitled "Dropout Detection in Continuous Analyte Monitoring Data During Data Excursions", the disclosures of each of which are incorporated herein by reference in their entirety for all purposes.

BACKGROUND

The detection of the concentration level of glucose or other analytes in certain individuals may be vitally important to their health. For example, the monitoring of glucose levels is particularly important to individuals with diabetes or pre-diabetes. People with diabetes may need to monitor their glucose levels to determine when medication (e.g., insulin) is needed to reduce their glucose levels or when additional glucose is needed.

Devices have been developed for automated in vivo monitoring of analyte time series characteristics, such as glucose levels, in bodily fluids such as in the blood stream or in interstitial fluid. Some of these analyte level measuring devices are configured so that at least a portion of the devices are positioned below a skin surface of a user, e.g., in a blood vessel or in the subcutaneous tissue of a user. As used herein, the term analyte monitoring system is used to refer to any type of in vivo monitoring system that uses a sensor disposed with at least a portion subcutaneously to measure and store sensor data representative of analyte concentration levels automatically over time. Analyte monitoring systems include both (1) systems such as continuous glucose monitors (CGMs) which transmit sensor data continuously or at regular time intervals (e.g., once per minute) to a processor/display unit and (2) systems that transfer stored sensor data in one or more batches in response to a request from a processor/display unit (e.g., based on an activation action and/or proximity using a near field communications protocol).

In some cases, analyte monitoring systems have been found to occasionally provide false low readings for relatively short periods (e.g., non-zero-mean signal artifacts). These false low readings, referred to as "dropouts," are distinct from a situation where no reading at all is provided. When no data at all is provided, an analyte monitoring system can easily detect that there is a problem because there simply is no signal from the sensor. In the case of a dropout however, there is still a signal and the data may appear to be correct but in fact, the data is temporarily incorrect. In a CGM for example, such false data can trigger an unnecessary low blood sugar (e.g., hypoglycemia event) false alarm. Thus, what is needed are systems, methods, and apparatus to reliably determine when a dropout has occurred in analyte monitoring system sensor data.

SUMMARY

The present invention provides systems, methods, and apparatus that allow a user to analyze a collection of analyte monitoring system sensor data to identify dropouts. By improving dropout identification capabilities, the present invention enables researchers to better understand dropout characteristics and thereby potentially develop a detection and correction algorithm that, for example, could be incorporated into a future analyte monitor system to detect and correct for dropouts as they are happening. In addition, improved dropout identification can facilitate research efforts to mitigate these errors and to provide a basis to compare sensor designs. Better dropout recognition may also allow healthcare providers and patients to calibrate analyte monitor system alarm thresholds more accurately to reduce false alarms. Embodiments of the present invention segments analyte monitoring system sensor data into time series associated with repeating events, such as meals, that cause analyte levels to vary over time. Using one or more of curve smoothing, time dilation, and dynamic range scaling techniques to normalize the data for comparison, two or more time series that correspond to the same repeating event (e.g., breakfast) on different days are compared. If a time series includes a period with an anomalous low level compared with the same period in another corresponding time series, the period is identified as a dropout.

Some embodiments of the present disclosure include computer-implemented methods of identifying a dropout in analyte monitoring system sensor data. The methods include receiving a signal representative of sensor data from an analyte monitoring system related to an analyte level of a patient measured over time; storing the sensor data in a computer system storage device; segmenting the sensor data into a plurality of time series wherein each time series is associated with a different instance of a repeating event; selecting a first time series to analyze for dropouts from the plurality of time series;

comparing the selected first time series to a second time series among the plurality of time series; determining whether the selected first time series includes a portion that is more than a predefined threshold lower than a corresponding portion of the second time series; and displaying, on a computer system display, an indication that the selected first time series includes a dropout if the selected first time series includes a portion that is more than the predefined threshold lower than the corresponding portion of the second time series. The invention also includes a computer system and a computer program product for identifying a dropout in analyte monitoring system sensor data. Numerous other aspects and embodiments are provided. Other features and aspects of the present invention will become more fully apparent from the following detailed description, the appended claims, and the accompanying drawings.

DETAILED DESCRIPTION

Figure 1:
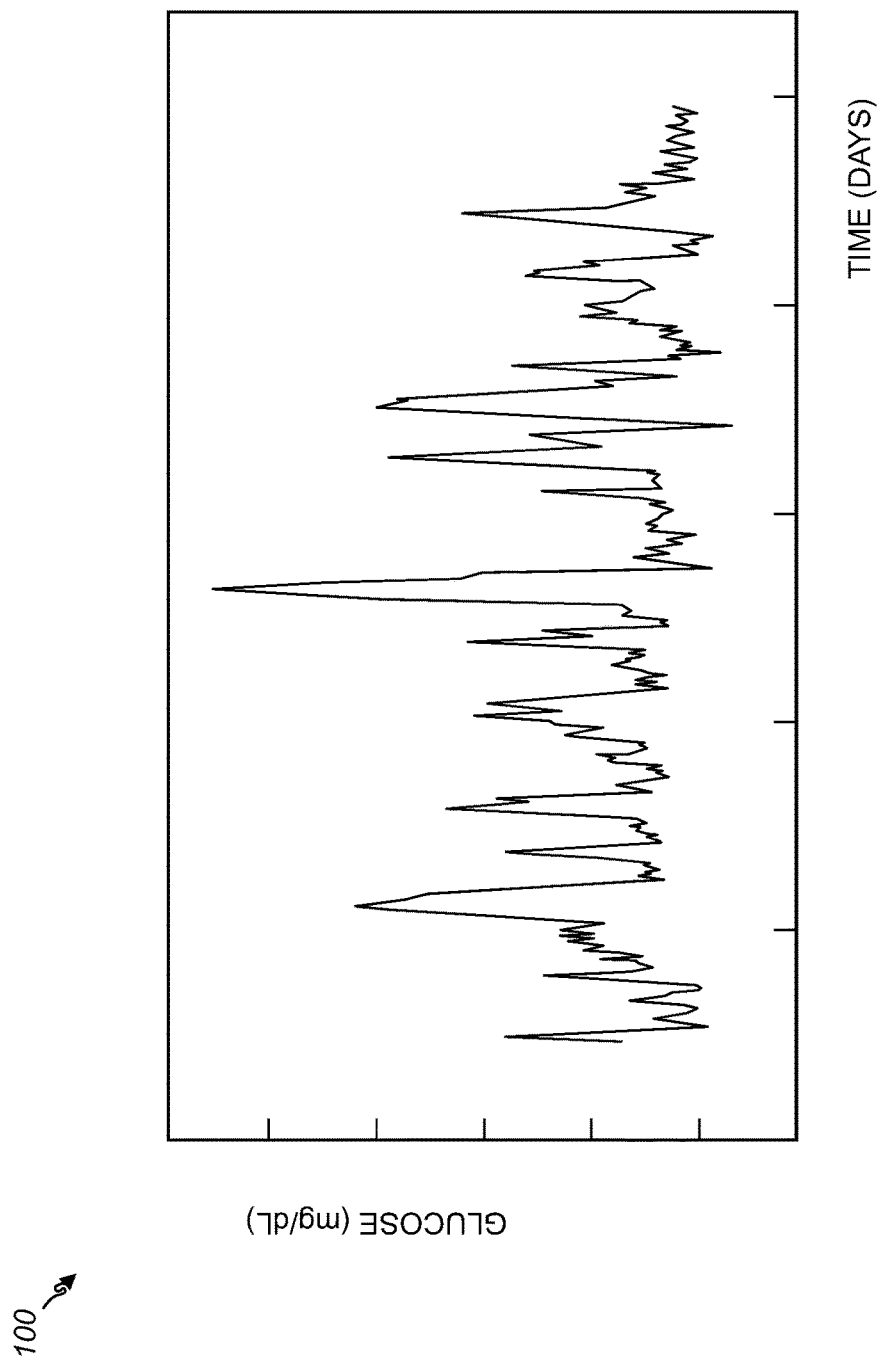
FIG. 1 depicts an example graph of analyte monitoring system sensor data plotted over time in accordance with some embodiments of the present invention.

The present invention provides systems, methods, and apparatus to identify dropouts in sensor data from an analyte monitoring system, such as, for example, any type of in vivo monitoring system that uses a sensor disposed with at least a portion subcutaneously to measure and store sensor data representative of analyte concentration levels automatically over time. Analyte monitoring systems may include CGMs which are programmed to transmit sensor data according to a predetermined transmission schedule, continuously, or at regular time intervals to a processor/display unit and systems that transfer stored sensor data in one or more batches in response to a request from a processor/display unit, i.e., not according to a predetermined transmission schedule. Without requiring a patient to wear two or more analyte sensors, the present invention is operable to identify dropouts in data from a single analyte sensor. According to some embodiments of the present invention, data representative of a patient's monitored analyte concentration level (herein referred to as "sensor data") previously captured over a period of time (e.g., two weeks) is segmented into time series representative of sensor data reflecting the effects of a meal or other repeating event that causes data "excursions" from a stable analyte concentration level. Several time series representing repeating events, for example, a meal, or an activity occurring at a fixed time of day, may be identified for comparative analysis. In some embodiments, event time markers, either manually input into the system or automatically determined from meal start estimates (without user intervention), may be used to identify the beginning and end of a time series. Once two or more time series have been identified as corresponding to different instances of the same repeating event, the corresponding time series can be analyzed to detect dropouts. In some embodiments of the present invention, corresponding time series are compared to identify low analyte level differences that represent dropouts. However, since a patient's analyte levels do not follow an identical pattern each day and since excursion events such as meals are longer or shorter on different days, data modulation algorithms or techniques may be employed to normalize data (time series normalized data) or otherwise process or transform data to match it to other time series data for comparison. Harmonizing sets of un-harmonized sensor data time series to each other enables similar data sets that are not exactly identical to be compared to each other. Time series modulation algorithms or techniques may employ one or more of time series curve smoothing, dynamic range matching, and time dilation, to aid in the comparison of the corresponding time series.

The invention may be applied to any analyte concentration level determination system that may exhibit or at least be suspected of exhibiting, or that may be susceptible to, dropouts. Embodiments of the invention are described primarily with respect to continuous glucose monitoring devices and systems but the present invention may be applied to other analytes and analyte characteristics, as well as data from measurement systems that transmit sensor data from a sensor unit to another unit such as a processing or display unit in response a request from the other unit. For example, other analytes that may be monitored include, but are not limited to, acetyl choline, amylase, bilirubin, cholesterol, chorionic gonadotropin, creatine kinase (e.g., CK-MB), creatine, DNA, fructosamine, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times. The present invention also provides numerous additional embodiments.

Embodiments of the present invention may include a programmed computer system adapted to receive and store data from an analyte monitoring system. The computer system may include one or more processors for executing instructions or programs that implement the methods described herein. The computer system may include memory and persistent storage devices to store and manipulate the instructions and sensor data received from the analyte monitoring system. The computer system may also include communications facilities (e.g., wireless and/or wired) to enable transfer of the sensor data from the analyte monitoring system to the computer. The computer system may include a display and/or output devices for identifying dropouts in the sensor data to a user. The computer system may include input devices and various other components (e.g., power supply, operating system, clock, etc.) that are typically found in a conventional computer system. In some embodiments, the computer system may be integral to the analyte monitoring system. For example, the computer system may be embodied as a handheld or portable receiver unit within the analyte monitoring system.

The various methods described herein for performing one or more processes also described herein may be embodied as computer programs (e.g., computer executable instructions and data structures) developed using an object oriented programming language that allows the modeling of complex systems with modular objects to create abstractions that are representative of real world, physical objects and their interrelationships. However, any practicable programming language and/or techniques may be used. The software for performing the inventive processes, which may be stored in a memory or storage device of the computer system described herein, may be developed by a person of ordinary skill in the art based upon the present disclosure and may include one or more computer program products. The computer program products may be stored on a computer readable medium such as a server memory, a computer network, the Internet, and/or a computer storage device.

Turning to FIG. 1, a graph 100 of glucose concentration level (mg/dL) over time (days) depicting an example of sensor data generated by an analyte monitoring system is shown. The graph 100 plots a patient's glucose level over the lifetime of the analyte monitoring system's sensor. For example, the particular example graph 100 shown represents data collected by an analyte monitoring system over five days. The variations in the patient's glucose level are referred to as excursions and the excursions may be associated with events in the patient's daily activities. In particular, meals cause excursions as the in-take of food affects the patient's glucose level. However, looking at the graph 100 in FIG. 1, it may not be easy to identify meal excursions because any eating patterns of the patient are not obvious when the data is plotted as one long sequence.

Figure 2:
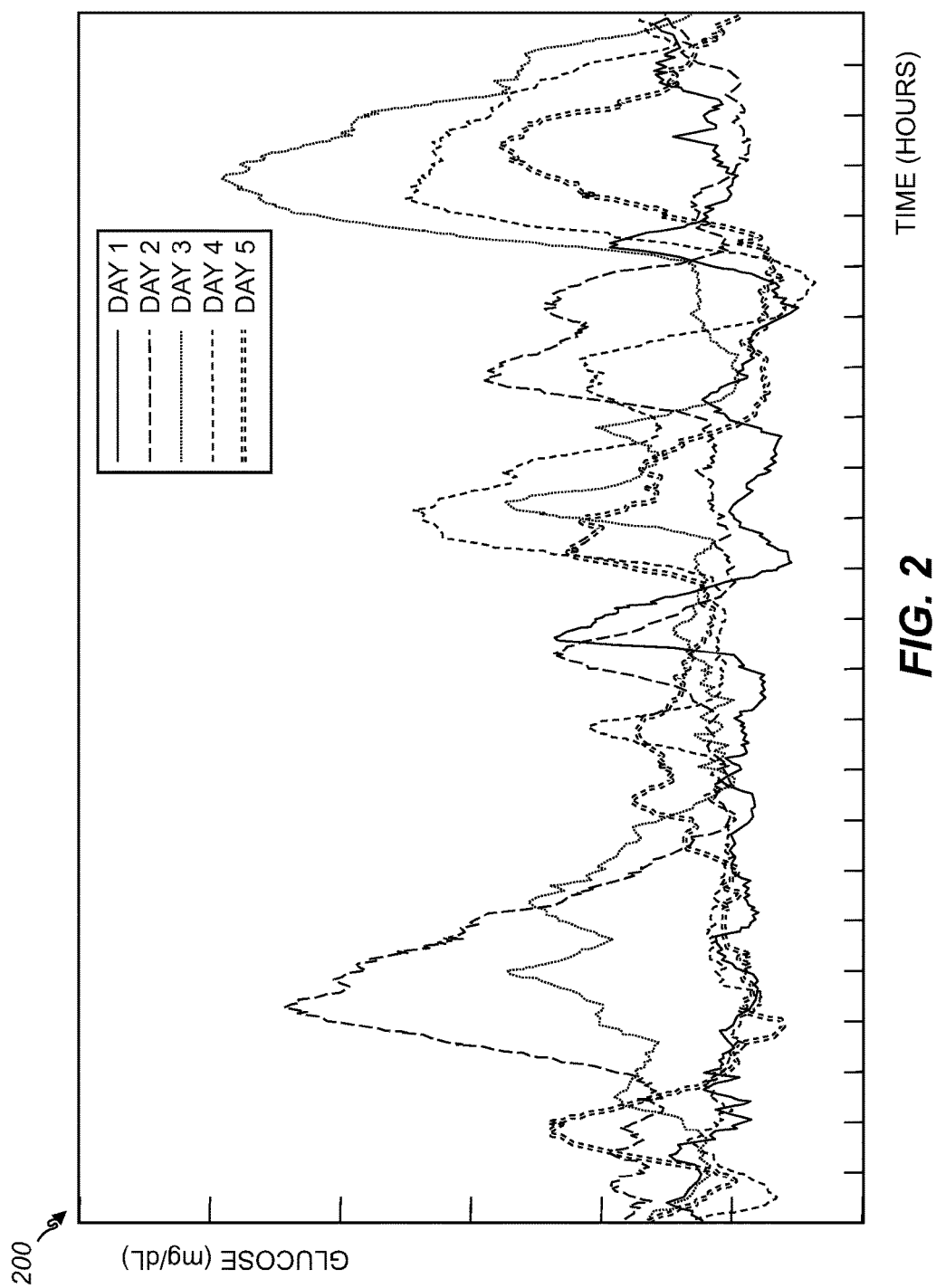
FIG. 2 depicts an example graph of segmented and overlaid analyte monitoring system sensor data plots in accordance with some embodiments of the present invention.

According to embodiments of the present invention, the sensor data may be segmented by the computer system into daily plots that are overlaid to reveal the patient's behavior patterns as shown in the graph 200 of FIG. 2. The overlaid plots may thus be used to identify meal excursions in the data. For example, in the particular graph 200 shown, the grouping of peaks at about 2 PM and about 8 PM suggest that these peaks correspond to daily meals consumed at roughly the same time each day wherein the 2 PM peaks correspond to lunch and the 8 PM peaks correspond to dinner.

In some embodiments, the plots of the sensor data may be, for example, sliding-average smoothed to remove "noise" and to facilitate easier comparison of the plots. In an unweighted sliding-average smoothing, each data point of the plot is replaced with the average of "m" adjacent points, where "m" is a positive integer referred to as the "smoothing width" or "smoothing window" in the case of a data plot over time as here. In some embodiments, various different smoothing windows (e.g., 15 minutes, 20 minutes, 30 minutes, etc.) may be tried by the computer system to find acceptable smoothening results while not significantly distorting features associated with true glucose excursions. For example, the smallest smoothing window that removes most of the jagged points on the curve without changing the overall shape of the curve may be selected. In some embodiments, other methods of smoothing may be used.

Once the overlaid daily plots are smoothed, they may be segmented into time series that correspond to repeating events (e.g., meals). A window of time may be defined where two or more time series of sensor data (e.g., x1, x2, x3, . . . , xN) from the same patient is to be compared. For example, the start of the time window for a repeating event that occurred on the last day of the sensor data may be determined using the latest meal marker (e.g., breakfast, lunch, dinner). This meal marker may be input by the user or determined by a meal start estimator. Details describing obtaining a meal marker from a meal start estimator may be found in U.S. Patent Application No. 61/582,209, filed Dec. 30, 2011, entitled "Method and Apparatus for Determining Medication Dose Information," which is hereby incorporated by reference. The end of the time window for a repeating event that occurred on the last day of the sensor data may be the latest available data from the sensor, or a time at which a new meal marker has been identified/provided. The start of the time window for a repeating event that occurred on previous days may be determined by meal markers from the appropriate prior days of the same type (e.g., breakfast matched with breakfast, or generic meal matched to the nearest time-of-day as provided by the analyte monitoring system's clock). Thus, using the smoothed, overlaid sensor data, the computer system may be programmed to identify two or more corresponding time series of sensor data that represent excursions resulting from the same repeating event occurring on different days.

Assuming the computer system identifies N pre-smoothed time series, there will be N−1 time series to compare against the x1 time series. Because patients' analyte levels do not follow an identical pattern day to day, and since each breakfast, lunch, or dinner may last longer or shorter than prior days' breakfast, lunch, or dinner, it may be helpful to perform some time dilation (or time stretching) functions on the sensor data to facilitate comparison between two different time series. Therefore, for each of the N−1 comparisons (e.g., x1 vs. x2; x1 vs. x3; . . . x1 vs. xN−1), the computer system may perform the following steps.

a. Set y1 equal to the x1 time series and define y2 to be the next time series to compare against (e.g., x2, x3, . . . , or xN−1).
b. Define a finite set of time dilation ($T_d$) parameters. For example: $T_d$={5/10, 6/10, 7/10, 8/10, 9/10, 1, 10/9, 10/8, 10/7, 10/6, 10/5}
   Where a $T_d$ range of a factor of two is selected as sufficient to cover the anticipated time span of variation between different excursions. Other values may be used.
c. For each $T_d$ value:
   i. Stretch or compress y2 by the $T_d$ value.
      For example, for $T_d$=5/10=1/2, the time series y2 is compressed to be half as short as the original. For $T_d$=10/5=2, the time series y2 is stretched to be twice as long as the original.
   ii. Compute y2', where the values are interpolated such that the time series y2' has the same sample time as y1. A linear interpolation method or any other practicable method of interpolation may be used.
   iii. Compute the cross correlation between y1 and y2'.
   iv. Repeat by using the next $T_d$ value in the set.
d. Find the $T_d$ value that results in the highest cross-correlation between y1 and y2'. The $T_d$ value that results in the highest cross-correlation between y1 and y2' is the best time dilation adjustment.
e. Pairing from the start of y1 and y2', and the subsequent samples, compute values at each time sample k:

$$r1(k)=y1(k)/y2'(k),$$

$$b1(k)=\mathrm{median}(\{r1(k-T_w), \ldots, r1(k+T_w)\})$$

$$n1(k)=r1(k)/b1(k)$$

where $T_w$ represents a time window large enough to enable the calculation of the patient's baseline glucose levels relative to each time instance k; and where n represents a baseline-normalized ratio between two sensor glucose values.
f. Any time period within the x1 time series with an n1 value below a predetermined threshold, n_low, may be identified as a dropout. The threshold n_low may be equal to a fixed amount, such as 0.95 for example, or in some embodiments, a variable amount based on an initial value (e.g., 0.95) that increases as a function of the latest sensor noise quality. Other values may be used.
g. Repeat the process by replacing y2=x2 with the next time series (e.g., set y2 equal to x3, x4, . . . , xN−1).

In another embodiment, curve smoothing, dynamic range matching, and time dilation are used to enable comparison of corresponding pre-smoothed time series. The addition of dynamic range matching scales the analyte concentration amplitudes to make comparison easier. For each of the N−1 comparisons (e.g., x1 vs. x2; x1 vs. x3; . . . x1 vs. xN−1), the computer system may perform the following steps.

a. Set y1 equal to the x1 time series and define y2 to be the next time series to compare against (e.g., x2, x3, . . . , or xN−1).
b. Determine the dynamic range of y1 time series by estimating upper (y1u), lower (y1l), and average (y1a) values.
   For example: sort all y1 values, and determine the $5^{th}$ and $95^{th}$ percentile values. Set y1u to the $95^{th}$ percentile value in y1, and set y1l to the $5^{th}$ percentile value in y1. Set y1a to the $50^{th}$ percentile value in y1. Other values may be used.

c. Calculate the dynamic range of y2 time series using the same method.
d. Adjust the dynamic range of y2 time series to match that of y1.
   For example, compute y2":=y1a+[[y2−y2a] [y1u−y1l]/ [y2u−y2l]]
e. Define a finite set of time dilation ($T_d$) parameters.
   For example: $T_d$={5/10, 6/10, 7/10, 8/10, 9/10, 1, 10/9, 10/8, 10/7, 10/6, 10/5}
f. For each $T_d$ value:
   i. Stretch or compress y2" by the $T_d$ value.
      For example, for $T_d$=5/10=1/2, the time series y2" is compressed to be half as short as its original. For $T_d$=10/5=2, the time series y2" is stretched to be twice as long as its original. Other values may be used.
   ii. Compute y2', where the values are interpolated such that the time series y2' has the same sample time as y1. A linear interpolation method or any other practicable method of interpolation may be used.
   iii. Compute the cross correlation between y1 and y2'.
   iv. Repeat by using the next $T_d$ value in the set.
g. Find the $T_d$ value that results in the highest cross-correlation between y1 and y2'. The $T_d$ value that results in the highest cross-correlation between y1 and y2' is the best time dilation adjustment.
h. Pairing from the start of y1 and y2', and the subsequent samples, compute values at each time sample $k: r1(k)=y1(k)/y2'(k),$ $b1(k)=\text{median}(\{r1(k-T_w), \ldots, r1(k+T_w)\})$ $n1(k)=r1(k)/b1(k)$ i. Any time period within the x1 time series with an n1 value below a predetermined threshold, n_low, may be identified as a dropout. The threshold n_low may be equal to a fixed amount, such as 0.95 for example, or in some embodiments, a variable amount based on an initial value (e.g., 0.95) that increases as a function of the latest sensor noise quality. Other values may be used.
j. Repeat the process by replacing y2=x2 with the next time series (e.g., set y2 equal to x3, x4, . . . , xN−1).

In some other embodiments, the process is similar to the two embodiments described above until the point in which a dropout is identified. Instead of identifying a dropout segment whenever any one of the comparator time series (x2, x3, . . . , xN−1) results in an n1 value below a predetermined threshold, a dropout segment is identified whenever any one of the comparator time series results in an n1 value below a predetermined threshold n_low and no other n1 at the same time period is higher than n_high where, for example, n_high equals approximately 1.2. Other values may be used.

Figure 3A:
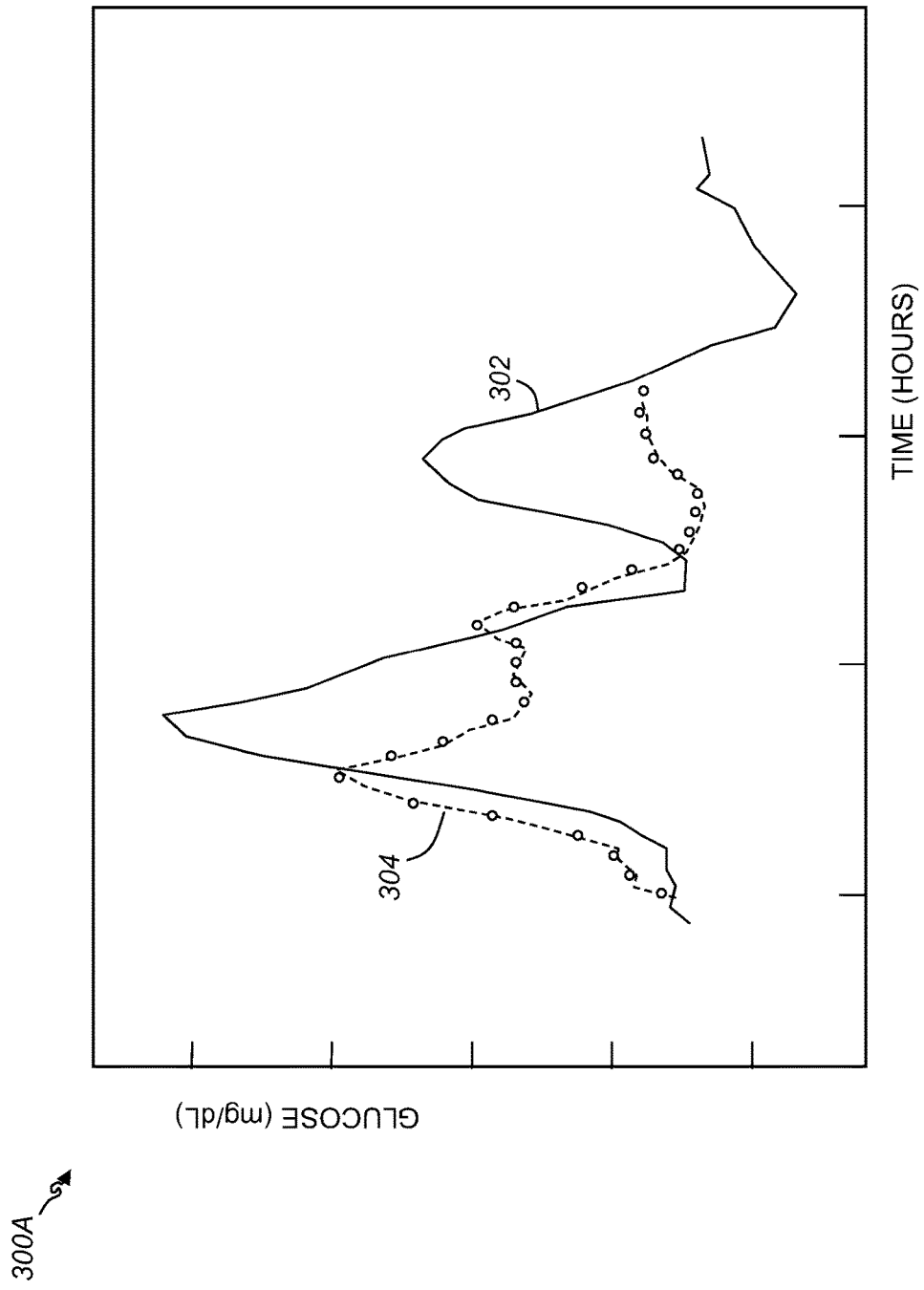
FIGS. 3A to 3D depict an example graph sequence of two smoothed time series plots of sensor data corresponding to the same repeating event occurring on different days, one having been time dilated and dynamic range adjusted, in accordance with some embodiments of the present invention.
Figure 3B:
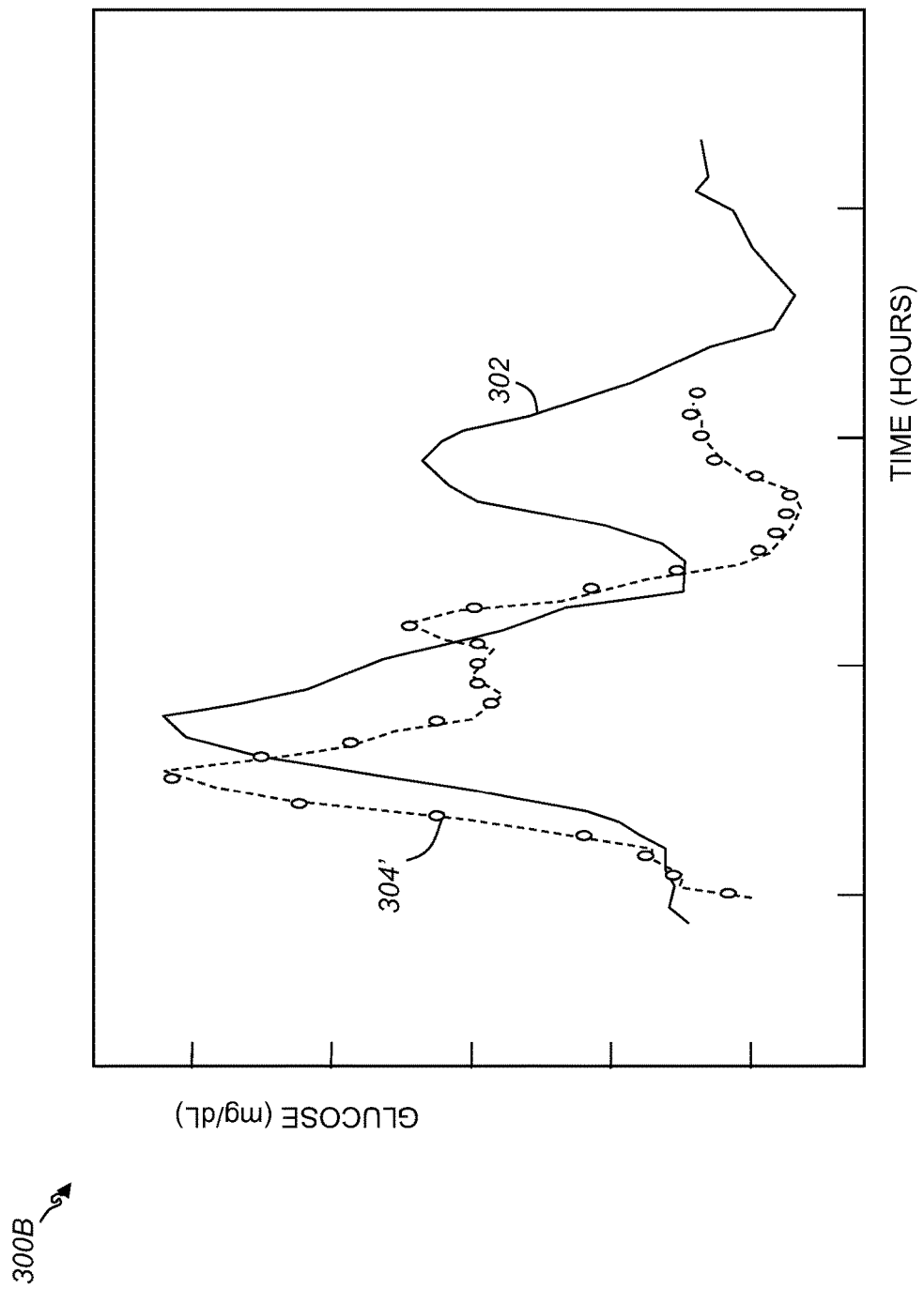

The above processes compare a most recent time series against all available corresponding time series to identify periods within the most recent time series that are dropouts. FIGS. 3A to 3D and 4A to 4C graphically depict simplified embodiments of this process. FIG. 3A depicts a graph 300A of a simple case where only two time series 302, 304 are to be compared to identify dropouts. The plots of the two time series 302, 304 have been smoothed as described above. Comparing the plots 302, 304 in FIG. 3A relative to each other, reveals that the analyte concentration data excursion caused by the event (e.g., a meal) associated with the plot 302 was larger than the analyte concentration data excursion caused by the event associated with the plot 304 (e.g., more carbohydrates were consumed during the meal associated with plot 302 than during the meal associated with plot 304). Thus, a dynamic range scaling operation as described above may be used to stretch plot 304 vertically to facilitate identification of any dropouts. An example of the results of the dynamic range scaling operation on the plot 304 is depicted in FIG. 3B.

Figure 3C:
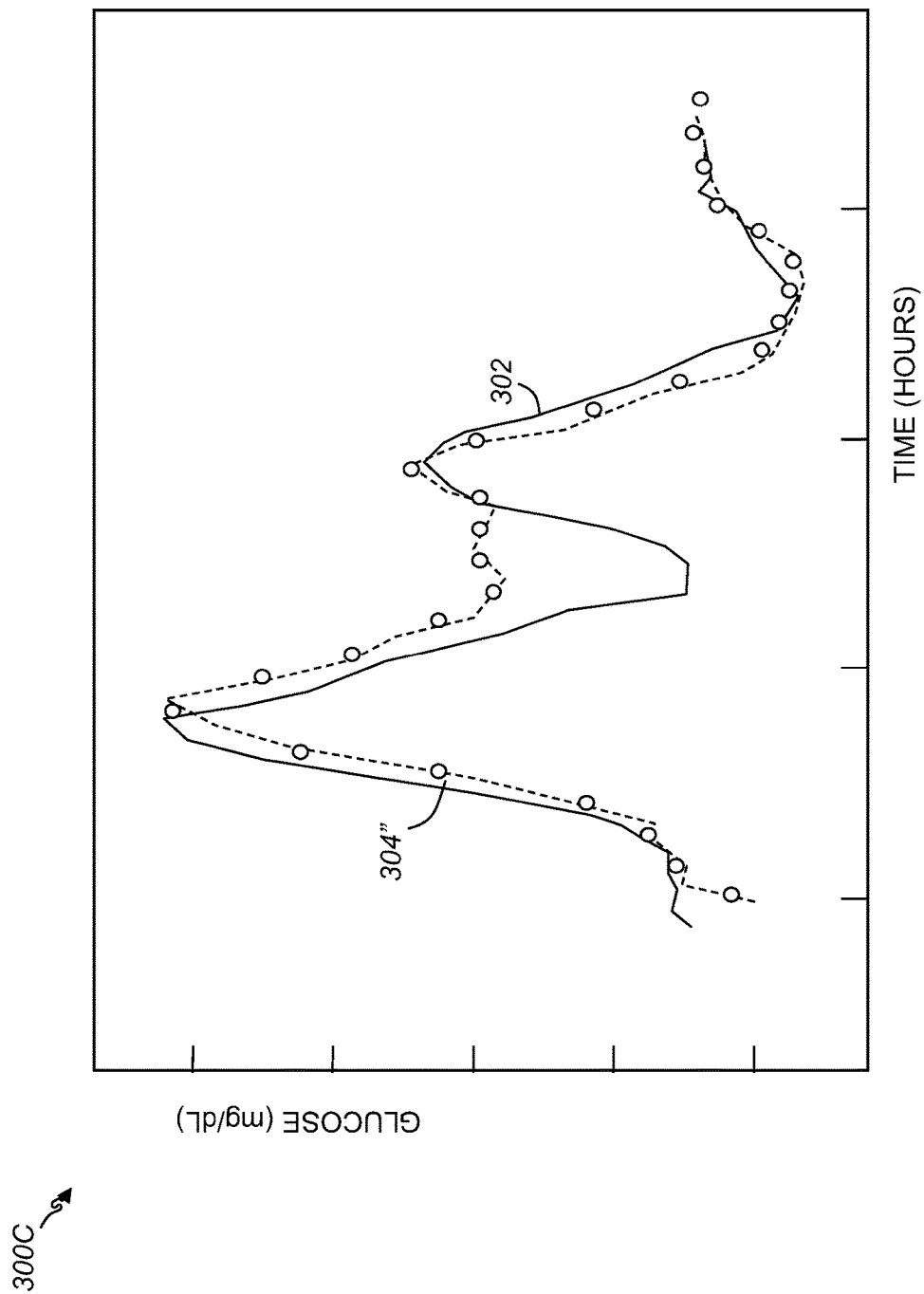

Analysis of FIG. 3B, which is a graph 300B, reveals that the repeating event associated with the plot 304 took less time than the event associated with the plot 302. Thus, a time dilation operation as described above may be used to stretch plot 304 laterally to facilitate identification of any dropouts. FIG. 3C is a graph 300C that illustrates an example of the results of the time dilation operation on the plot 304.

Figure 3D:
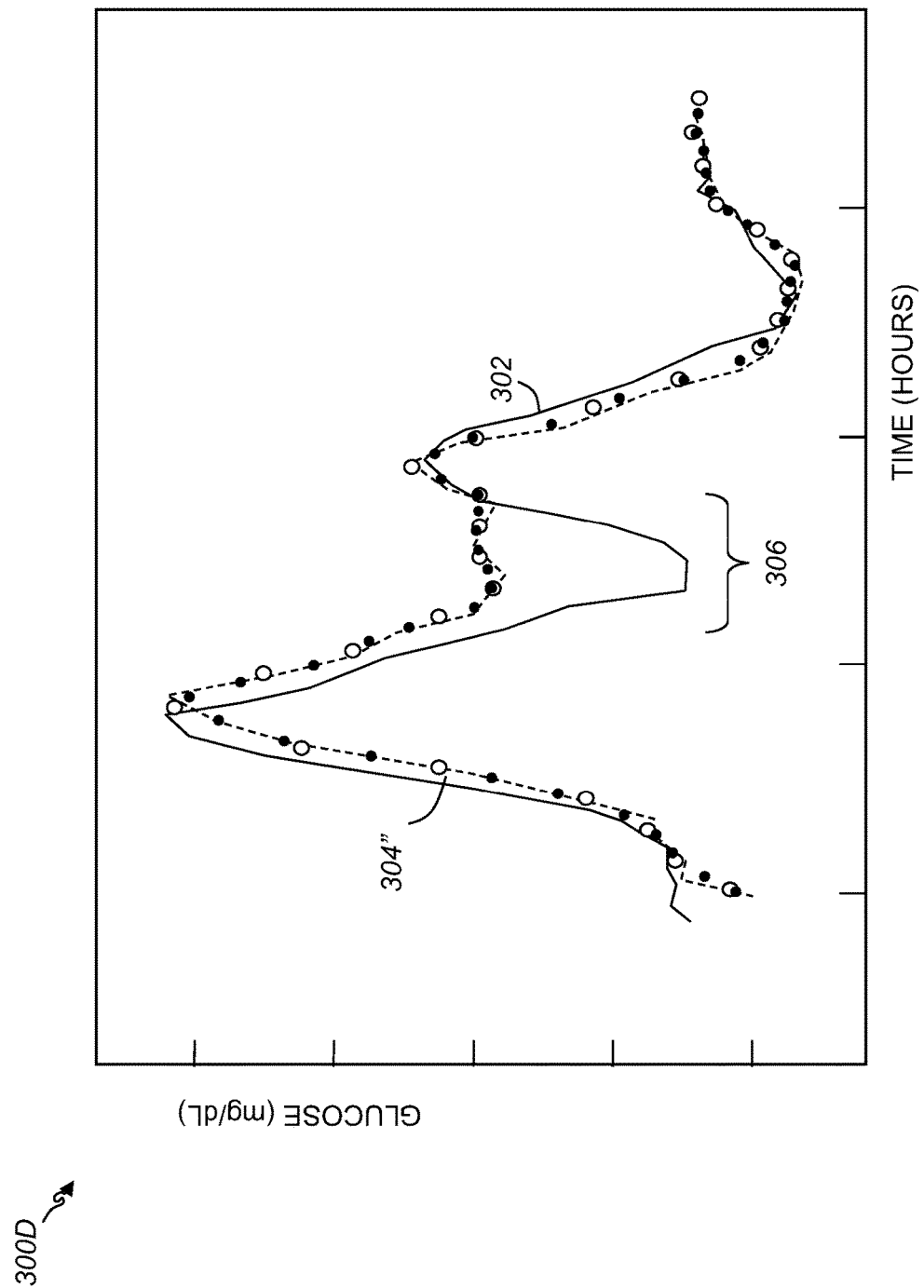

FIG. 3D is a graph 300D that represents the results of dynamic range scaling and time dilating of plot 304 so that it best matches (e.g., has the highest cross-correlation with) plot 302. In other words, plot 304" represents the dynamic range scaled and time dilated version of plot 304 that most closely correlates (e.g., overlaps) with plot 302. With the two plots 302, 304 smoothed, plot 304 dynamic range scaled to plot 304' and time dilated to plot 304", the period labeled 306 can easily be identified as a dropout in plot 302. In some embodiments, the computer system may provide the user with a display similar to the graph 300D of FIG. 3D with an indication that the time period 306 represents a dropout.

Figure 4A:
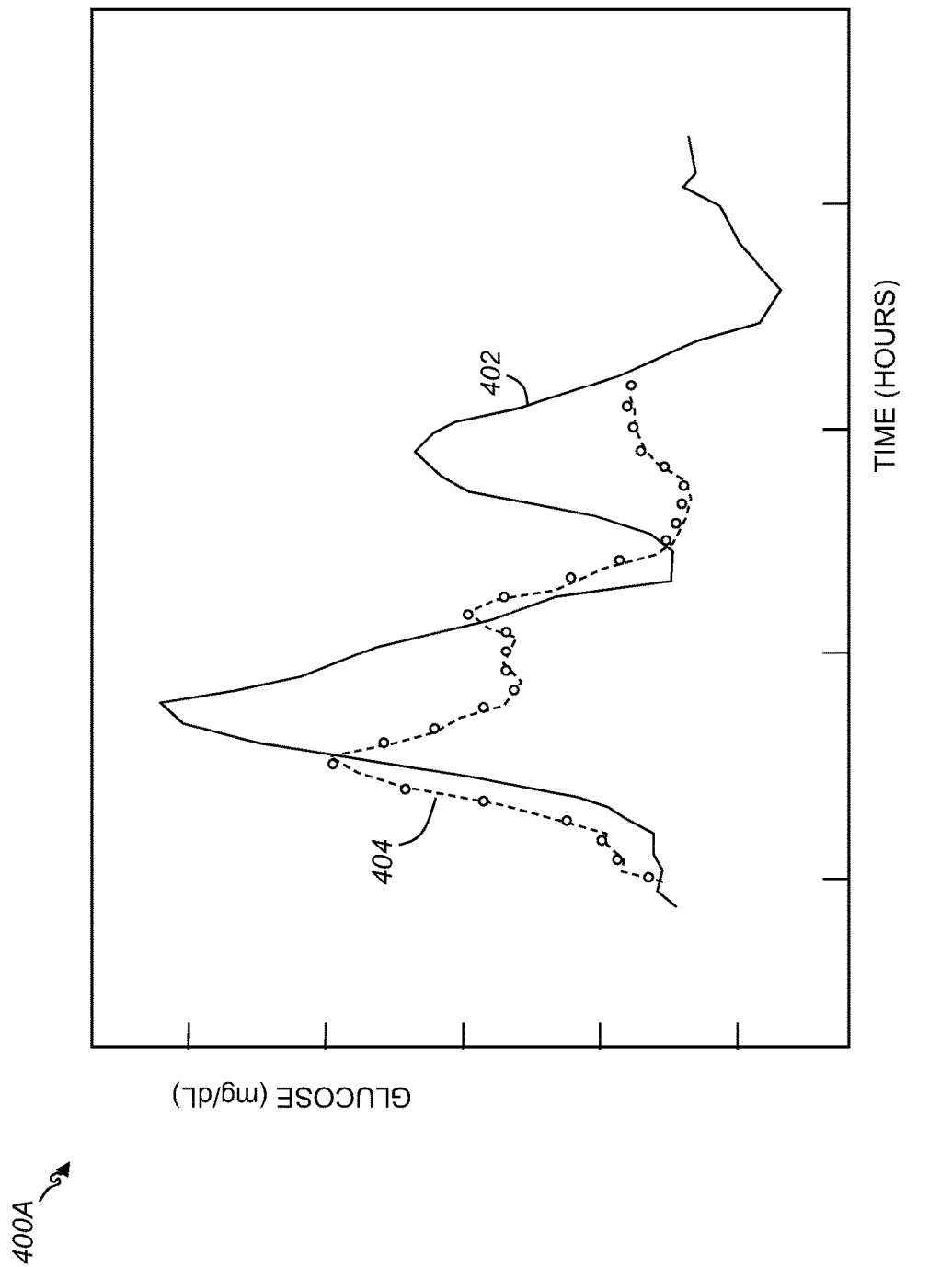
FIGS. 4A to 4C depict an example graph sequence of two smoothed time series plots of sensor data, one having been time dilated in accordance with some embodiments of the present invention.
Figure 4B:
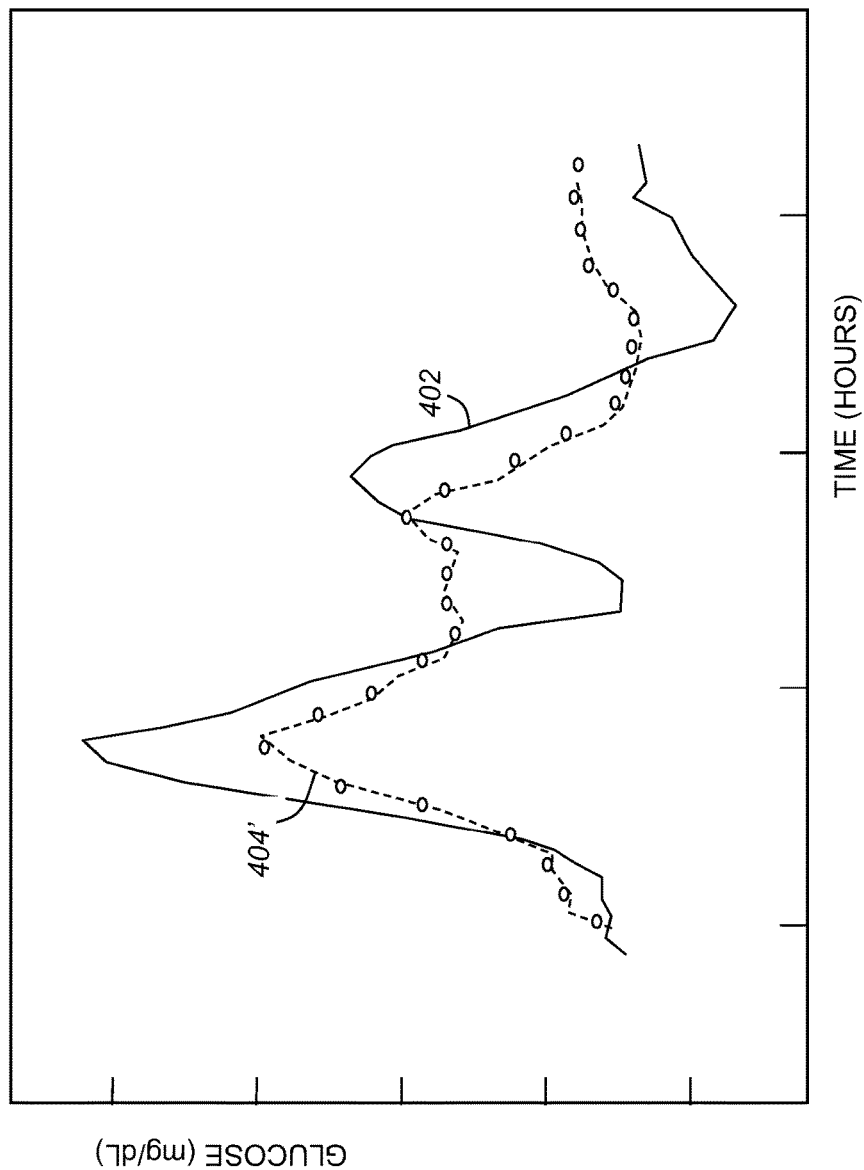

FIG. 4A depicts a graph 400A of another simple case where only two time series 402, 404 are to be compared to identify dropouts. The plots of the two time series 402, 404 have been smoothed as described above. Comparing the plots 402, 404 in FIG. 4A relative to each other, reveals that the repeating event associated with the plot 404 took less time than the event associated with the plot 402. Thus, a time dilation operation as described above may be used to stretch plot 404 laterally to facilitate identification of any dropouts. FIG. 4B illustrates an example of the results of the time dilation operation on the plot 404.

Figure 4C:
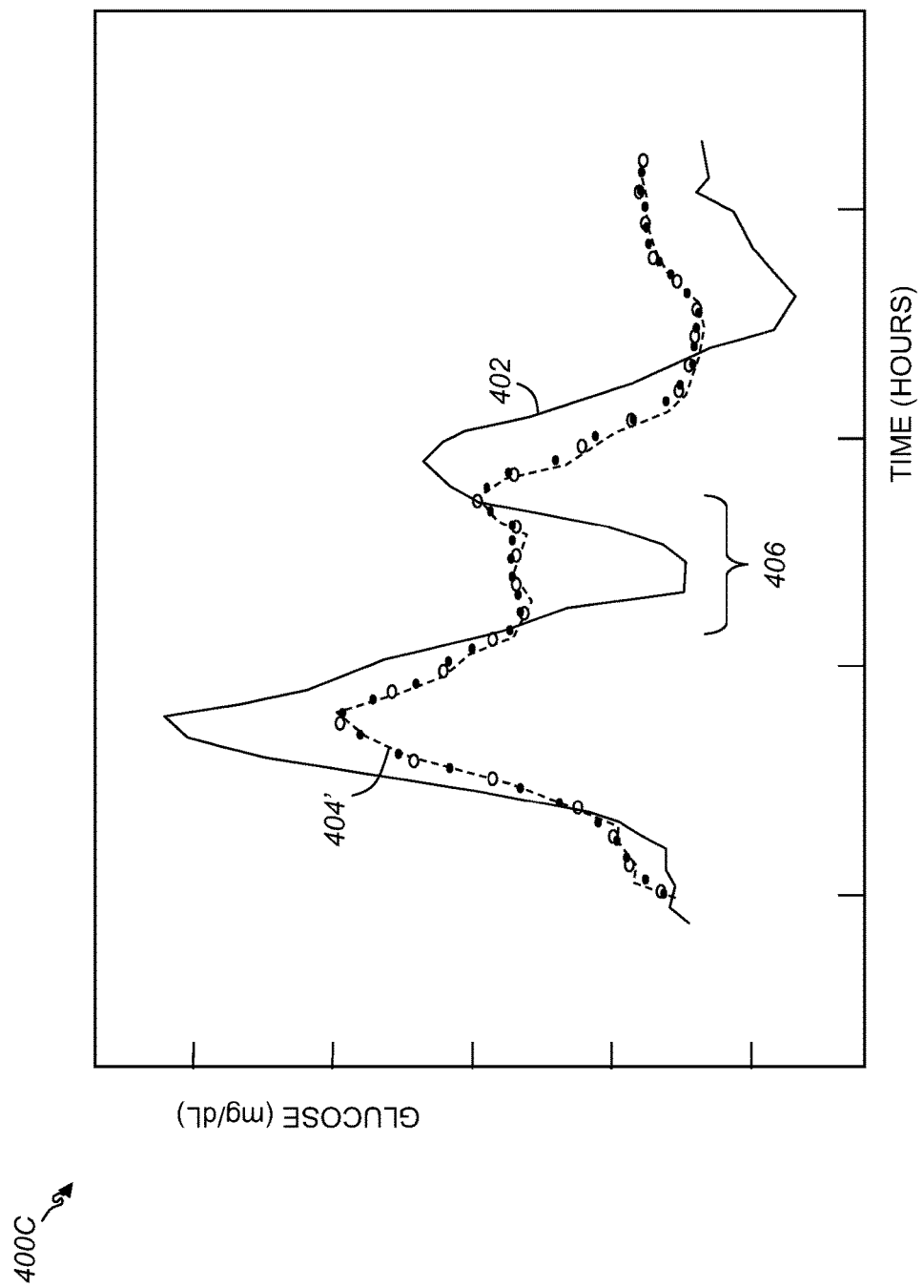

From the graph 400B in FIG. 4B, a dropout can be identified as described above, without having to perform dynamic range scaling operation. Thus, FIG. 4C is a graph 400C that represents the results of time dilating plot 404 so that it best matches (e.g., has the highest cross-correlation with) plot 402. In other words, plot 404' represents the time dilated version of plot 404 that most closely correlates (e.g., overlaps) with plot 402. With the two plots 402, 404 smoothed and plot 404 time dilated to plot 404', the period labeled 406 can easily be identified as dropout in plot 402. In some embodiments, the computer system may provide the user with a display similar to the graph 400C of FIG. 4C with an indication that the time period 406 represents a dropout.

Figure 5:
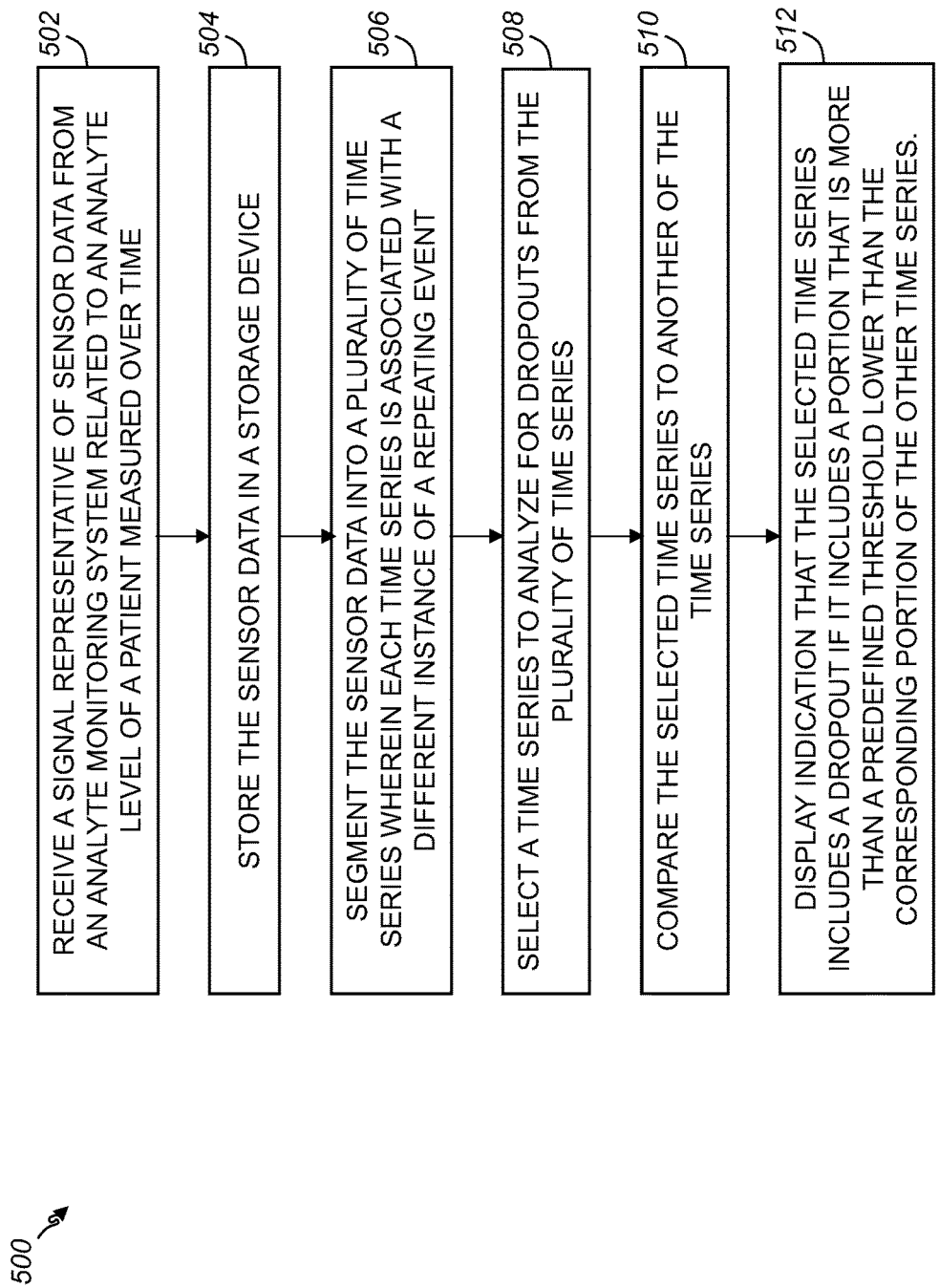
FIG. 5 depicts a flow chart illustrating an example method in accordance with some embodiments of the present invention.

Turning now to FIG. 5, a flow chart illustrating an example method 500 of the present invention is provided. In some embodiments, a signal representative of sensor data is received by the computer system from an analyte monitoring system, for example, a CGM (502). The sensor data may include a historical record of an analyte level of a patient measured over time. The sensor data is stored in a storage device of the computer system (504). In some embodiments, the sensor data is segmented into a plurality of time series (506). Each time series is associated with a different instance of a repeating event. In some embodiments, the sensor data may be smoothed as described above, to facilitate the segmenting. In some embodiments, a meal start time may be identified for each of the time series to facilitate identifying the start and end of the time series. The meal start time may be manually entered (e.g., based on information provided by the patient) or automatically determined using estimating software as mentioned above.

Once one of the time series is selected to be analyzed for dropouts (508), the selected time series may be compared to at least one of the other time series (510). In some embodiments, time dilation and dynamic range matching techniques as described above may be performed on the time series used for comparison to aid in correlating the two time series and to compensate for different lengths of time and different magnitudes of the associated events. The computer system determines whether the selected time series includes a portion that is more than a predefined threshold lower than a corresponding portion of the time series used for comparison (512). The predefined threshold may be selected as described above. If there is a portion of the selected time series that is lower than the comparison time series by more than the threshold amount (e.g., a negative glucose level difference larger than x amount), the computer system displays an indication that the selected time series includes a dropout. In some embodiments, the sensor data that represents the dropout may be removed, set to a zero value, or otherwise marked as invalid data. In some embodiments, the dropout sensor data may be replaced with interpolated data.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

What is claimed is:

1. A method of identifying a signal dropout in analyte sensor data, comprising:
   segmenting sensor data into a plurality of time series;
   generating a plurality of plots for each time series of the plurality of time series;
   generating a visual depiction of an analyte concentration over a period of time by at least overlaying each plot of the plurality of plots on each other to form a graph associating the analyte concentration with one or more user behaviors over the period of time;
   determining an appropriate smoothing window from a plurality of smoothing windows, by at least determining that smoothing the graph using the appropriate smoothing window would not change an overall shape of the graph more than an acceptability threshold;
   smoothing the graph using the appropriate smoothing window to obtain a smoothed graph;
   displaying the visual depiction, including the smoothed graph, on a computer system display;
   selecting a first time series to analyze for dropouts from the plurality of time series;
   comparing the selected first time series to a second time series among the plurality of time series, based on the smoothed graph;
   determining that the selected first time series includes a portion that is more than a predefined threshold lower than a corresponding portion of the second time series, based on the smoothed graph;
   identifying a location on the smoothed graph corresponding to the portion that is more than the predefined threshold lower than the corresponding portion of the second time series; and
   displaying, on the computer system display, an indication that the identified location on the smoothed graph includes a dropout.

2. The method of claim 1, wherein segmenting the sensor data further comprises identifying a meal start time during each one of the plurality of time series.

3. The method of claim 1, wherein comparing the selected first time series further comprises time dilating the second time series.

4. The method of claim 1, wherein comparing the selected first time series further comprises time dilating and dynamic range adjusting the second time series.

5. The method of claim 4, wherein the graph includes a plot for the time dilated and dynamic range adjusted second time series.

6. The method of claim 1, wherein displaying the indication that the identified location on the smoothed graph includes the dropout further comprises displaying an indication of a period of time on the graph associated with the dropout.

7. The method of claim 1, wherein comparing the selected first time series further comprises normalizing the first time series to the second time series using at least one of dynamic range matching and curve smoothing.

8. The method of claim 1, wherein each time series is associated with a different instance of a repeating event.

9. An apparatus for identifying a signal dropout in sensor data, comprising:
   a display;
   a processor operatively coupled to the display; and
   a memory coupled to the processor, the memory storing processor executable instructions to:
   segment sensor data into a plurality of time series;
   generate a plurality of plots for each time series of the plurality of time series;
   generate a visual depiction of an analyte concentration over a period of time by at least overlaying each plot of the plurality of plots on each other to form a graph associating the analyte concentration with one or more user behaviors over the period of time;
   determine an appropriate smoothing window from a plurality of smoothing windows, by at least determining that smoothing the graph using the appropriate smoothing window would not change an overall shape of the graph more than an acceptability threshold;
   smooth the graph using the appropriate smoothing window to obtain a smoothed graph;
   provide the visual depiction, including the smoothed graph, on the display;
   select a first time series to analyze for dropouts from the plurality of time series;
   compare the selected first time series to a second time series among the plurality of time series, based on the smoothed graph;
   determine that the selected first time series includes a portion that is more than a predefined threshold lower than a corresponding portion of the second time series, based on the smoothed graph;
   identify a location on the smoothed graph corresponding to the portion that is more than the predefined threshold lower than the corresponding portion of the second time series; and provide, on the display, an indication that the identified location on the smoothed graph includes a dropout.

10. The apparatus of claim 9, wherein the instructions to segment the sensor data further comprise instructions to identify a meal start time during each one of the plurality of time series.

11. The apparatus of claim 9, wherein the instructions to compare the selected first time series further comprise instructions to time dilate the second time series.

12. The apparatus of claim 9, wherein the instructions to compare the selected first time series further comprise instructions to time dilate and dynamic range adjust the second time series.

13. The apparatus of claim 12, wherein the graph includes a plot for the time dilated and dynamic range adjusted second time series.

14. The apparatus of claim 9, wherein the instructions to provide the indication that the identified location on the smoothed graph includes the dropout further comprise instructions to display an indication of a period of time on the graph associated with the dropout.

15. The apparatus of claim 9, wherein comparing the selected first time series further comprises normalizing the first time series to the second time series using at least one of dynamic range matching and curve smoothing.

16. The apparatus of claim 9, wherein each time series is associated with a different instance of a repeating event.

17. The method of claim 1, wherein determining the appropriate smoothing window comprises determining that the appropriate smoothing window would facilitate comparison of an appearance of the plot for the selected first time series to an appearance of the plot for the second time series, wherein smoothing the graph comprises smoothing the plot for the selected first time series and smoothing the plot for the second time series, and wherein comparing the selected first time series to the second time series comprises comparing the smoothed plot for the selected first time series to the smoothed plot for the second time series.

18. The apparatus of claim 9, further storing instructions to determine the appropriate smoothing window by at least determining that the appropriate smoothing window would facilitate comparison of an appearance of the plot for the selected first time series to an appearance of the plot for the second time series, to smooth the graph by at least smoothing the plot for the selected first time series and smoothing the plot for the second time series, and to compare the selected first time series to the second time series by at least comparing the smoothed plot for the selected first time series to the smoothed plot for the second time series.

19. The method of claim 1, wherein determining that smoothing the graph using the appropriate smoothing window would not change the overall shape of the graph more than the acceptability threshold comprises determining that the appropriate smoothing window would remove one or more points determined to be jagged.

20. The apparatus of claim 9, further storing instructions to determine that smoothing the graph using the appropriate smoothing window would not change the overall shape of the graph more than the acceptability threshold comprises determining that the appropriate smoothing window would remove one or more points determined to be jagged.

* * * * *